United States Patent
Brulez et al.

(10) Patent No.: US 7,494,506 B2
(45) Date of Patent: Feb. 24, 2009

(54) METHOD FOR FIXING TRACTION THREADS TO ENDS OF A PROSTHETIC LIGAMENT

(75) Inventors: Bernard Brulez, Bourbonne-les-Bains (FR); Jacques-Philippe Laboureau, Le Tignet (FR)

(73) Assignee: Lars-Laboratoire d'Application et de Recherche Scientifique, Arc sur Tille (FR)

(*) Notice: Subject to any disclaimer, the term of this patent is extended or adjusted under 35 U.S.C. 154(b) by 395 days.

(21) Appl. No.: 10/586,362
(22) PCT Filed: Jan. 21, 2005
(86) PCT No.: PCT/FR2005/000142
§ 371 (c)(1),
(2), (4) Date: Jul. 18, 2006
(87) PCT Pub. No.: WO2005/079707
PCT Pub. Date: Sep. 1, 2005

(65) Prior Publication Data
US 2007/0118217 A1     May 24, 2007

(30) Foreign Application Priority Data
Jan. 23, 2004    (FR)   ................... 04 00630

(51) Int. Cl.
*A61F 2/08* (2006.01)
(52) U.S. Cl. .................. 623/13.11; 623/13.2
(58) Field of Classification Search ..... 623/13.2–13.15; 606/86, 99
See application file for complete search history.

(56) References Cited

U.S. PATENT DOCUMENTS

| 3,176,316 | A | * | 4/1965 | Bodell ................ 623/13.19 |
| 4,668,233 | A | * | 5/1987 | Seedhom et al. ......... 623/13.11 |
| 5,800,543 | A | * | 9/1998 | McLeod et al. ............ 623/13.2 |
| 6,203,572 | B1 | | 3/2001 | Johnson et al. |
| 6,752,831 | B2 | * | 6/2004 | Sybert et al. ............. 623/13.17 |

* cited by examiner

*Primary Examiner*—Suzette J Gherbi
(74) *Attorney, Agent, or Firm*—Young & Thompson

(57) ABSTRACT

Method for production of a prosthetic ligament (1), for the replacement of a natural joint ligament, having a global cylindrical form and including a medial intra-articular section (3) between two intra-osseous end parts (2). The method includes a step of the rolling or folding on itself of a web of synthetic polymer fibers, followed by a step of installation of a traction thread (5) to each of the ends (4) of the ligament (1), then a step of placing a tip (6) on the ends (5), characterized in that the placing of the tip (6) includes producing a radial ligature (60) of the ligament (1) provided with the traction threads (5), by of a ligature thread (7).

7 Claims, 2 Drawing Sheets

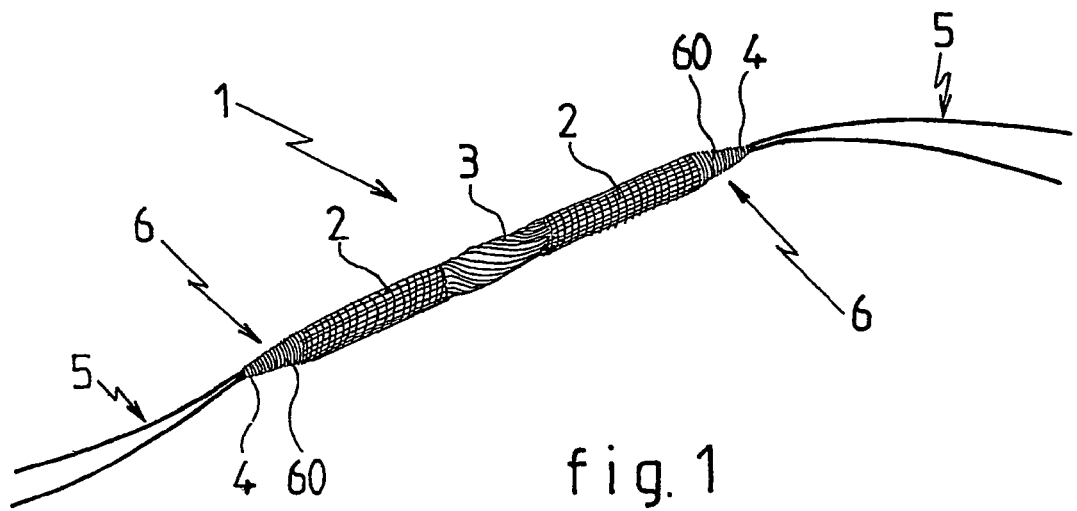
fig. 1
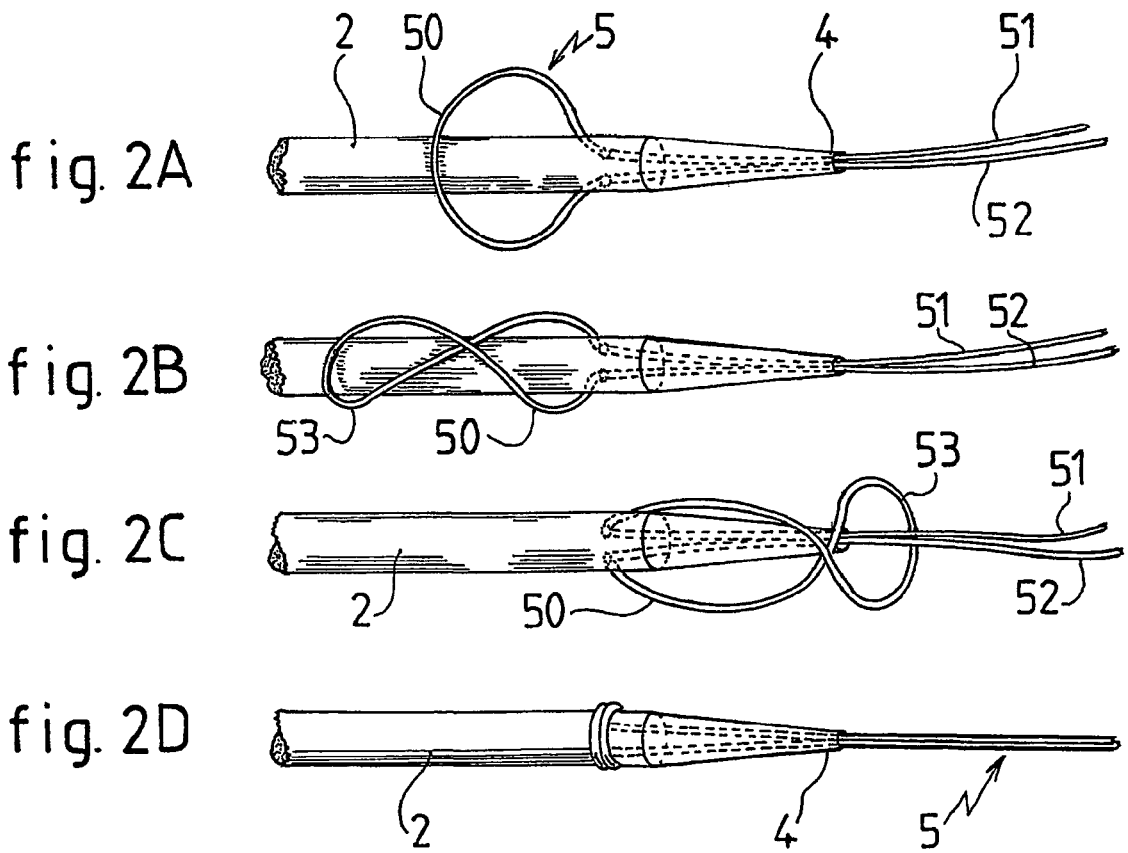
fig. 2A
fig. 2B
fig. 2C
fig. 2D

METHOD FOR FIXING TRACTION THREADS TO ENDS OF A PROSTHETIC LIGAMENT

This present invention concerns a process for the fixing of traction threads to the ends of a prosthetic ligament for the replacement of biological articular ligaments, and in particular those of the knee, and the ligament thus obtained.

Most artificial ligaments are currently manufactured by the winding or folding onto itself of a web of synthetic polymer fibres, generally polyethylene terephtalate. These ligaments have the overall shape of extended cylinders having an intra-articular middle part between two intra-osseous end parts. Examples of such ligaments are to be found in particular in patents FR 2.755.846 and FR 2.697.151.

In order to facilitate the passage of these ligaments into the osseous tunnels, and to ensure that they are correctly secured, the ligaments are fitted at their ends with traction threads. These traction threads are fitted to the ligaments by making a loop with a thread at a certain distance from their free ends, gripping the ligament radially; the two strands of this thread are introduced into the thickness of the ligament and emerge at the free end of the ligament to which the said thread is fixed, after having pulled the two strands in the thickness of the ligament in a direction generally parallel to the longitudinal axis of the ligament. Then the two strands are knotted together at the point where they emerge from the ligament.

In order to protect the free ends of the ligament, to guide its passage in the osseous tunnels, and to avoid any movement of the traction threads when they are subjected to traction force, various solutions for ferrules have been invented by the manufacturers of ligaments. In the present text, the term "ferrule" refers to any part used to cap the ends of the traction threads of a prosthetic ligament.

A first example of these solutions consists of clamping the ligament underneath a loop of the traction thread with a ring, usually metal. Now these rings often get trapped in the osseous tunnels, and have difficulty getting around corners, making the fitting of such ligaments rather difficult and sometimes delicate.

A second solution is to fit onto the end of the ligament, a polyethylene cap which is equipped with a hole in its bottom through which the strands of the traction thread pass. The two strands of the traction thread are knotted together just as they emerge from the cap, immobilising the latter and preventing the thread from slipping. Although these caps are less problematic than the rings, they remain hard to use in some circumstances, such as in the case of replacing crossed ligaments behind the knee for example. In addition, these caps are sometimes associated with a ring, thus increasing the risk of inflammation because of the different nature of the materials used.

A third solution used by certain manufacturers consists of polymer film plastic (PVC) sheaths enclosing the end of the ligament, which are open at the point of emergence of the strands of traction thread. These sheaths can be created by thermoforming, for example. They have the drawback of being long and relatively rigid, making it difficult to pass the ligament in the osseous tunnels.

Finally, another solution employs silicone guides, moulded around the traction thread and having the shape of an extended cone. Though these guides have the required flexibility, they lose material in the osseous tunnels and give rise to blockages, because of their large size. Moreover, the lost particles present a risk of inflammatory reaction.

This present invention therefore aims to remedy these problems by proposing a process for the creation of a prosthetic ligament, including a stage of winding or folding onto itself of a web of synthetic polymer fibres, followed by a stage for the fitting of a traction thread to each of the ends of the ligament, and then a stage for the installation of a ferrule on the ends, remarkable in that the stage for installation of the ferrule consists of effecting a radial ligature of the ligament equipped with its traction threads by means of a ligature thread.

The expression "ligature thread" in the present text refers to a textile thread whose technical characteristics mean that it is intended to be used normally for the creation of ligatures.

It can be seen that such a ferrule, consisting of a ligature, is flexible and creates no excess thickness on the end of the ligament; it thus removes the difficulties of fitting the ligament, in particular when passing into the osseous tunnels and more especially around corners, whatever their configuration.

In addition, according to an essential characteristic of the invention, the ligature thread is chosen in the same material as that of the synthetic fibres constituting the web. The risks of inflammatory reaction in the patient are therefore considerably reduced since the ferrule is of same nature as the material constituting the ligament and that, moreover, the loss of particles of material is extremely low, or even non-existent. Note also the certain economic advantage of using the same raw material.

The resistance and the solidity of the ligatures and other knots, when they are effected correctly, is well known.

Other advantages and characteristics will emerge more clearly from the description that follows of a succession of stages of the process, provided by way of non-limiting examples, for the assembly of traction threads on a prosthetic ligament, after winding or folding onto itself of a polymer fibre web, with reference to the appended figures in which:

FIG. 1 is a schematic view in perspective of an artificial ligament.

FIG. 2 represents the sequence of a variant according to the invention for fitting the traction thread to the end of a ligament;

Figure 3A:
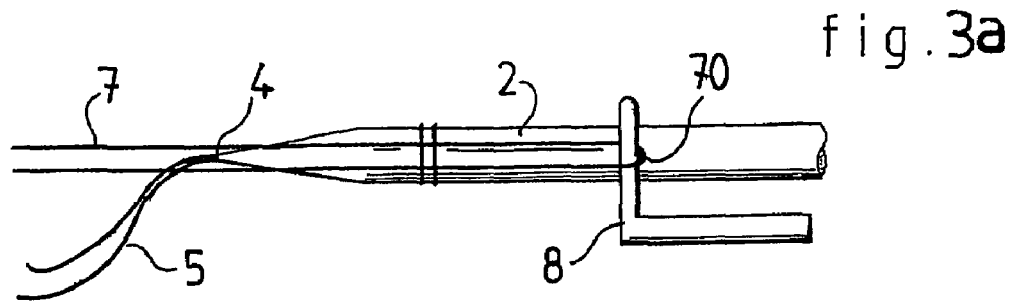
FIG. 3 represents the sequence of a method of implementation of the ligature constituting a flexible ferrule according to the invention.

Referring to FIG. 1, an artificial ligament 1 has the overall shape of an extended cylinder that includes an intra-articular middle part 3 between two intra-osseous end parts 2. The ligament is equipped at each of its ends 4 with traction threads 5, with the ends being capped by a ferrule 6, which in this case is a ligature 60, created according to the process detailed below. These artificial ligaments are created by the winding or folding on itself of a synthetic polymer fibre web, generally in polyethylene terephtalate. This web is cut and shaped in order to bring the ends 4 of the ligament 1 to the wanted shape, and then wound. Examples of ligaments of this type, with details of their creation process, can be found in patents FR 2.755.846 or FR 2.697.151 for example. Finally, the shape thus given to the ligament 1 is fixed by longitudinal stitching of the ligament.

This is followed by installation of the traction threads 5, which are necessary for fitting of the ligament to the patients, in order to enable the surgeon to perform the passage of the ligament in the osseous tunnels, as well as positioning it correctly and setting the tension required for the repair.

With reference to FIG. 2, and according to a characteristic of the invention, the installation of the traction thread 5 at the end of the ligament is effected in a sequence of stages, illustrated in FIGS. 2A to 2D. The first stage of the sequence consists of taking a traction thread 5, and then forming a loop 50 around the body of the ligament 1, without crossing the strands around the latter, and positioning the said loop 50 at a certain distance from the end 4 of the ligament 1. This distance varies generally from 20 to 50 mm from the end, according to the type of ligament concerned. For example, in the case of a ligament whose ends have a conical shape, this distance generally varies between 30 and 40 mm.

The two free strands 51, 52 of the traction thread are then taken and inserted and at diametrically opposite sides of the loop 50 into the thickness of the ligament 1. They are then pushed toward the outside of the ligament, toward the end 4 concerned, parallel to the longitudinal direction of the ligament. Care is taken during this stage not to reduce the size of the loop 50.

As illustrated in FIG. 2B, a twist is then given to the loop 50 so as to form a figure of eight whose base is anchored in the ligament and which forms a second loop 53 corresponding to the small part of the figure of eight. Then the end 4 of the ligament with the free strands 51, 52 is inserted into the second loop 53 and the first and second loops formed into a figure of eight are reduced so that they are positioned at the point of introduction of the two free strands of threads into the ligament. Finally, the knot thus formed is tightened by pulling on the strands 51, 52 of the traction thread 5.

In a manner which is optional and advantageous, an end stitch is then executed on the end 4 of the ligament, at the section of the ligament in which the two strands 51, 52 pass into the thickness of the ligament. This end stitch is intended to prevent any slippage of the traction thread 5 when the latter is subjected to a high traction force, in particular during the fitting of the ligament. The end stitch is executed, for example, with a sewing machine that includes an end-stitch program. Of course it is possible to use a different procedure for the installation of the traction thread, but the method which has just been described here has the advantage of being extremely simple and fast, and of not requiring any additional knots after fitting the ferrule that protects the end of the ligament.

With reference to FIG. 3, and according to another important characteristic of the invention, the next stage of installation of a ferrule 6 on the ends 4 of the ligament 1 equipped with its traction threads 5 consists of making a radial ligature 60 of the said ligament with a ligature thread 7.

This ligature 60 is created in accordance with the sequence illustrated bin FIGS. 3A to 3E.

The first stage for creation of the ligature 60 consists of forming an extended loop 70, from a ligature thread 7 drawn from a reel of thread, and positioning the said loop 70 onto the ligament 1, with the two strands of the ligature thread being parallel to the ligament and emerging at the end 4 of the ligament at which the said ligature 60 has been positioned. The ligament 1 is laid flat, preferably held by means of an appropriate device, and the loop 70 is advantageously held against the ligament by a removable bracket 8. This removable bracket 8 forms part of the aforementioned device for holding the ligament 1 flat. It also enables the operator to be freed, before creating the ligature 60, from the need, for example, to hold the loop 70 against the ligament 1 with one finger when executing the following stages of ligature creation.

Figure 3B:
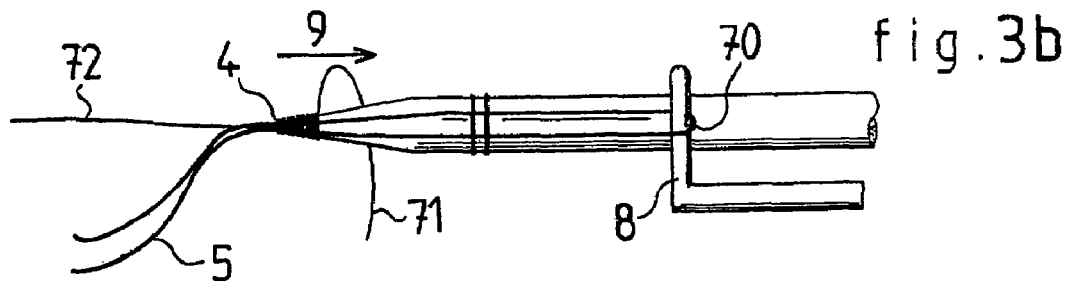

One of the strands of the thread 7 is then taken, and this becomes the running strand 71, and this is wound simultaneously around the ligament, around the second strand 72, known as the dormant strand, always positioned parallel to the longitudinal direction of the ligament 1, and around the loop 70, starting from the end 4 of the ligament and in moving in the direction of the intra-articular middle part 3, along the direction indicated by arrow 9 (FIG. 3B). Care is taken when winding the running strand 71 to form carefully adjacent turns.

Figure 3C:
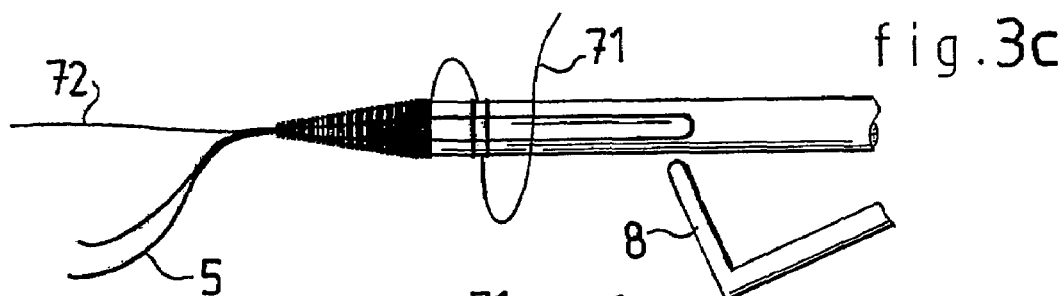

The running strand 71 is then passed into the loop 70 and the latter is removed from the bracket 8 which is holding it in position, as shown in FIG. 3C. Generally, this stage is effected when the turns formed have covered the double knot of the traction thread 5, at the point of insertion of the strands 51, 52 of the said thread 5 into the thickness of the ligament 1. Of course, it will be possible to reduce or increase the area covered by the turns, and therefore the size of the ligature 60, according to the needs specific to each type of prosthetic ligament, without moving outside the scope of the invention however.

Figure 3D:
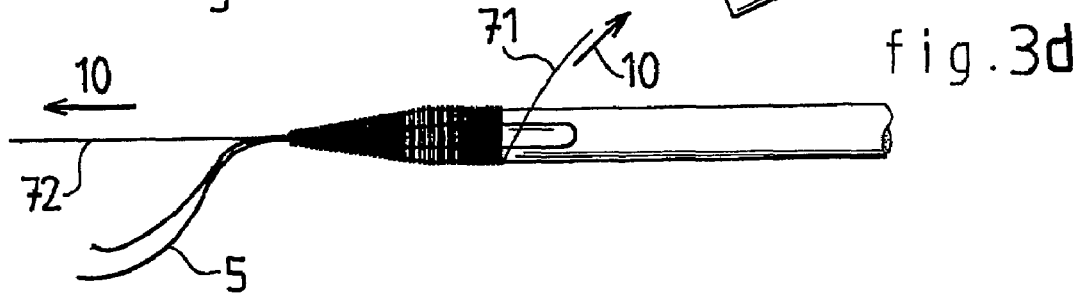

The assembly is then strongly tightened by pulling on the dormant strand 72 and the running strand 71 in the directions shown by arrows 10 in FIG. 3D, respectively in the longitudinal axis of the ligament for the dormant strand 72 and generally perpendicular to the latter for the running strand 71, taking care to keep the turns closely wound.

Figure 3E:
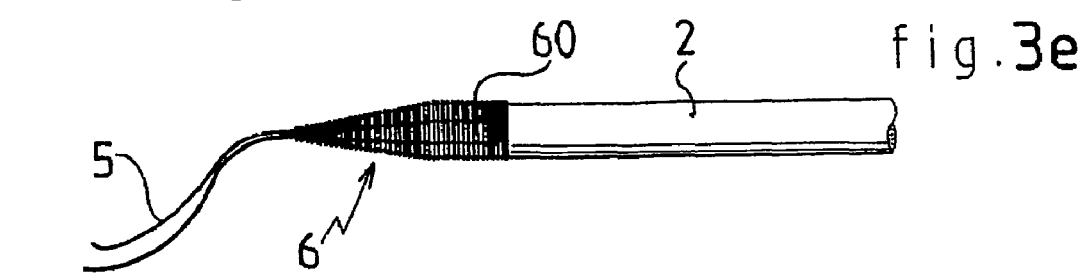

Finally, the two strands are cut flush with the ligature 60 and thus the ferrule 6 is created according to the invention, as represented in FIG. 3E.

According to another characteristic of the invention, the ligature thread 7 is chosen in the same material as that of the synthetic fibres constituting the web of the ligament 1. This material is usually polyethylene terephalate.

Finally, it goes without saying that the process according to the invention can be adapted to any forms of ligament other than those described, and the examples provided above are particular illustrations which are in no way limiting in relation to the areas of application of the invention.

The invention claimed is:

1. A process for the creation of a prosthetic ligament (1) for the replacement of a natural articular ligament, with an overall cylindrical shape, and that includes an intra-articular middle part (3) between two intra-osseous end parts (2), where this process includes a stage for winding or folding a web of synthetic polymer fibres onto itself, followed by a stage for fitting a traction thread (5) to each of the ends (4)of the ligament (1), and then a stage for installation of a ferrule (6) on the ends (5) characterized in that the installation of the ferrule (6) consists of making a radial ligature (60) of the ligament (1) equipped with its traction threads (5) with a ligature thread (7).

2. A process according to claim 1, characterized in that the fitting of the traction thread (5) is effected according to the following sequence:

take a traction thread (5) and form a loop (50) without crossing the strands around the ligament (1) and position it around the ligament, at a certain distance from one end (4) of the latter;

in diametric opposition on the loop (50), insert the two free strands (51, 52) of the traction thread (5) into the thickness of the ligament (1) and draw them toward the end (4) concerned, parallel to the longitudinal direction of the ligament (1) toward the outside;

make a twist in the loop (50) so as to form a figure of eight whose base is anchored in the ligament (1) and pass the end (4) of the ligament (1) with the free strands (51, 52) of the traction thread (5) into the second loop (53), that is to say into the small part of the figure of eight;

bring the two loops (50, 53) to the point of introduction of the free strands (51, 52) into the ligament (1);

tighten by pulling on the strands (51, 52) of the traction thread (5).

3. A process according to claim 1, characterized in that after the fitting of the traction thread (5), at least one end stitch is formed on the section of the ligament (1) into which the two strands (51, 52) of the traction thread (5) pass.

4. A process according to claim 1, characterized in that the ligature (60) is created in accordance to the following sequence:
- with a ligature thread (7), form an extended loop (70) and position it onto the ligament (1) which is laid flat, with the two strands of the thread (7) being parallel to the ligament (1) and emerging at the end (4) of the ligament (1) at which the ferrule (6) is positioned,
- hold the loop (70) firmly against the ligament (1),
- take one of the strands, which becomes the running strand (71), and simultaneously wind it around the ligament (1), around the dormant strand (72) and around the loop (70), starting from the end (4) of the ligament and moving in the direction of the intra-articular middle part (3), forming carefully adjacent turns,
- pass the running strand (71) into the loop (70),
- tighten hard by pulling on the dormant strand (72) and the running strand (71), taking care to keep the turns adjacent,
- cut the two strands (71, 72) flush with the ligature.

5. A process according to claim 1, characterized in that the ligature thread (7) is chosen in the same material as that of the synthetic fibres constituting the web.

6. A ligament (1) for the replacement of a natural articular ligament, with an overall cylindrical shape and that includes an intra-articular middle part (3) between two intra-osseous end parts (2), equipped with traction threads (5) at its ends (4) which are capped by a ferrule (6), characterized in that this is achieved by implementation of the process according to claim 1.

7. A process according to claim 2, characterized in that after the fitting of the traction thread (5), at least one end stitch is formed on the section of the ligament (1) into which the two strands (51, 52) of the traction thread (5) pass.

* * * * *